United States Patent [19]

Sheehan et al.

[11] Patent Number: 5,507,748
[45] Date of Patent: Apr. 16, 1996

[54] ACETABULAR PROSTHETIC APPARATUS AND TECHNIQUES

[75] Inventors: James M. Sheehan, County Dublin, Ireland; Neil Buckley, Wiltshire, England

[73] Assignee: Bristol-Myers Squibb Company, New York, N.Y.

[21] Appl. No.: 109,416

[22] Filed: Aug. 19, 1993

[30] Foreign Application Priority Data

Aug. 19, 1992 [GB] United Kingdom .................. 9217639

[51] Int. Cl.⁶ .................................................. A61B 17/88
[52] U.S. Cl. .................................. 606/94; 606/92; 623/22
[58] Field of Search ............................... 606/91, 94, 92, 606/99, 93, 1, 53, 86, 102, 105, 166, 191; 623/22, 18, 23; 220/287

[56] References Cited

U.S. PATENT DOCUMENTS

| | | | |
|---|---|---|---|
| 2,078,211 | 4/1937 | Williams | 220/287 |
| 2,736,536 | 2/1956 | Banowitz | 220/287 |
| 3,655,089 | 4/1972 | Tower | 220/287 |
| 3,889,665 | 6/1975 | Ling et al. | 606/91 |
| 4,305,394 | 12/1981 | Bertuch, Jr. | |
| 4,488,549 | 12/1984 | Lee et al. | |
| 4,563,778 | 1/1986 | Roche et al. | 623/22 |
| 4,711,233 | 12/1987 | Brown | 606/91 |
| 4,716,894 | 1/1988 | Lazzeri et al. | 606/91 |
| 5,098,437 | 3/1992 | Kashuba et al. | 606/89 |
| 5,147,366 | 9/1992 | Arroyo et al. | 606/94 |

FOREIGN PATENT DOCUMENTS

| | | | |
|---|---|---|---|
| 1932 | of 1903 | United Kingdom | 220/287 |
| 1563334 | 3/1980 | United Kingdom . | |

Primary Examiner—Guy Tucker
Attorney, Agent, or Firm—Todd A. Dawson

[57] ABSTRACT

A cement retaining shield for use when seating an acetabular prosthetic implant into a cement filled acetabulum. The shield includes at least two leaf-like sections which may be displaced outwardly by rotation of a cam to cover a substantial portion of the patient's acetabulum. The device is particularly useful in applying force through the shield to compress the cement into the acetabulum to improve bonding at the cement-bone interface and at the cement-implant interface. Preferably, the shield is in the form of a planar disc and the leaf-like sections are positioned in overlying relationship to the disc. The sections, responsive to the rotation of a cam, may be extended outwardly of the disc.

15 Claims, 3 Drawing Sheets

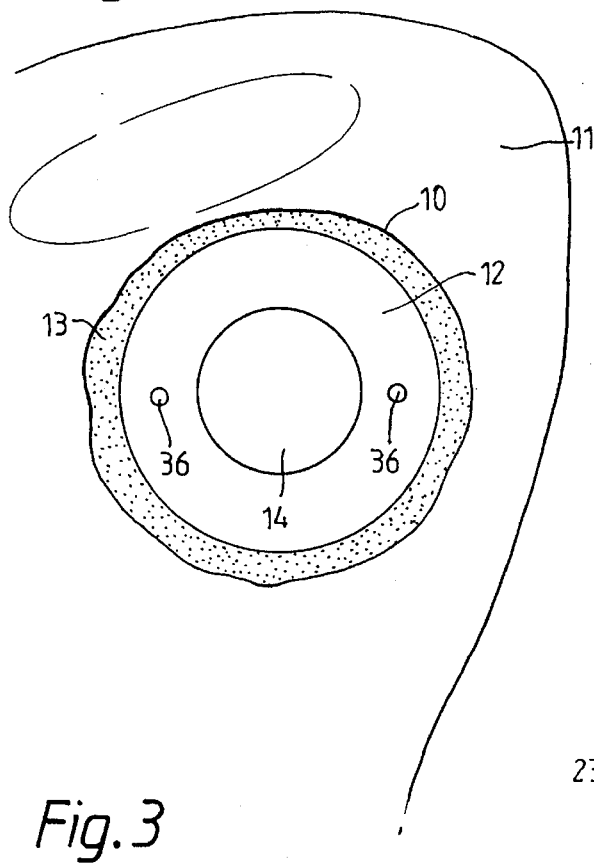
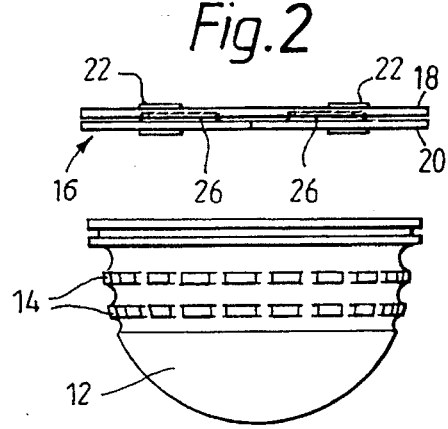
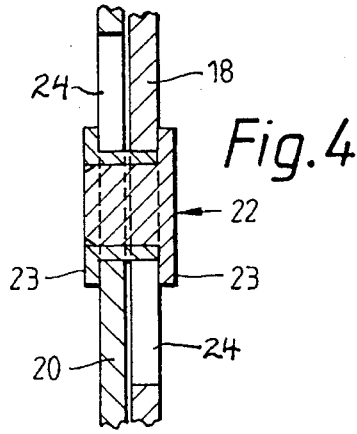
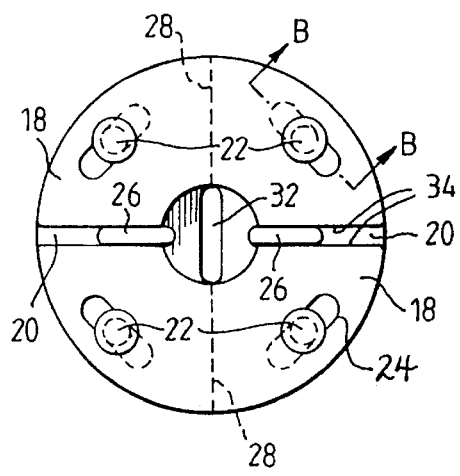
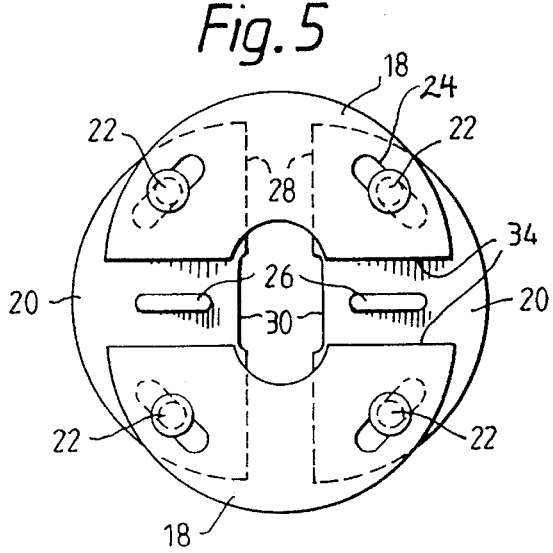

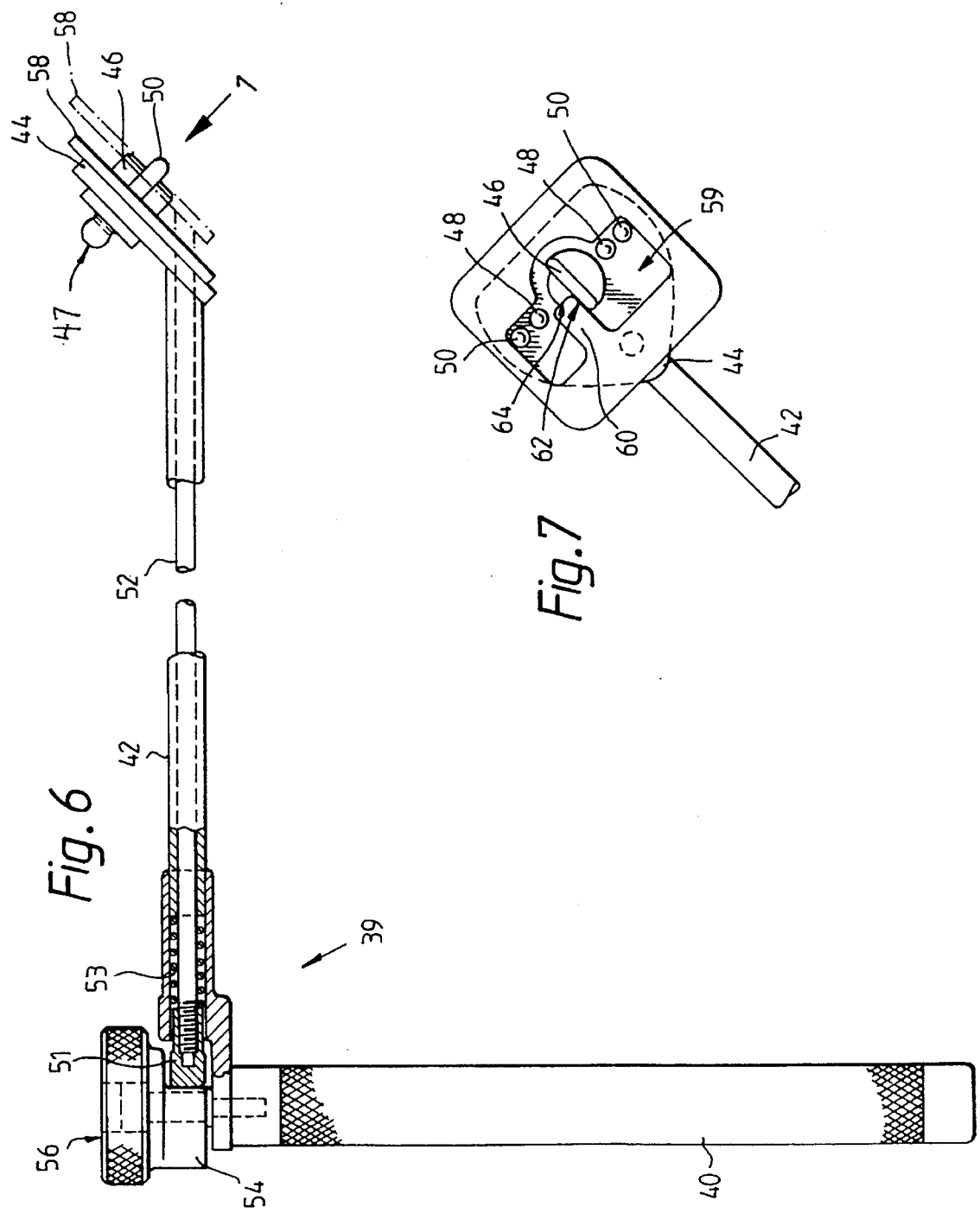

ACETABULAR PROSTHETIC APPARATUS AND TECHNIQUES

BACKGROUND OF THE INVENTION

This invention relates to acetabular prosthetic techniques, and in particular to a method of fitting an acetabular prosthesis, to apparatus for fitting an acetabular prosthesis, and to acetabular prosthetic systems.

A common failure mode of acetabular components of total hip replacement prostheses is loosening between the bone cement/acetabulum interface.

The bone cement/acetabulum interface could be improved if the bone cement is made to penetrate and fill interdigitions generated in the subcondral bone of the acetabulum.

A number of attempts have been made to improve the pressurisation of bone cement in the acetabulum. The most successful has probably been the Charnley Ogee acetabular cup which features a fixed flange attached to the cup. This flange is trimmed in the operating theatre to fit the patient's acetabulum, with the intention of thereby reducing egress of the uncured cement when it is compressed by pressure on the acetabular prosthesis. The disadvantage of this system is the difficulty of templating the acetabulum and the inherent high cost the flanged component.

OBJECTS AND SUMMARY OF THE INVENTION

One object of the present invention is to provide an acetabular prosthetic technique in which these disadvantages are overcome or at least reduced.

In one aspect the invention provides a method of fitting an acetabular prosthesis comprising placing bone cement in a subcondral acetabular recess, inserting the acetabular prosthesis therein, disposing an adjustable shield over the prosthesis, adjusting the size of the shield substantially to cover the recess so as to contain the cement therein and compressing said cement to improve bonding of the prosthesis to the recess.

Force may be applied through the shield to compress the cement.

In a second aspect the invention provides apparatus for use in fitting an acetabular prosthesis comprising a shield adapted to be positioned over a prosthesis to be placed in uncured bone cement in a subcondral acetabular recess, said shield being adjustable so as substantially to cover the recess and retain the cement therein whilst the cement is compressed to improve bonding of the prosthesis to the recess.

The shield may comprise a plurality of overlapping sections displaceable outwardly from the centre of the shield to adjust the size thereof.

In a preferred form the shield is a substantially planar disc, the sections being slideably and pivotally connected to each other.

In a third aspect the invention provides an acetabular prosthetic system comprising an acetabular prosthesis adapted to be placed in uncured bone cement in a subcondral acetabular recess, in combination with a shield as set forth above.

There may be locating means enabling the shield and the prosthesis to be located relative to each other.

A system according to the invention may also comprise adjusting means for adjusting the size of the shield and compression means for compressing the cement.

The adjusting means may comprise a rotatable cam adapted to enter the centre portion of the shield.

The locating means may comprise apertures in the shield through which fixed structure of the adjusting means engages the prosthesis.

The compression means may include means for rotating the cam and for applying force to the shield and the prosthesis via the fixed structure of the adjusting means.

There preferably are means for separating the adjusting means from the prosthesis and the shield after compression of the cement.

The separating means may comprise a part moveable away from the fixed structure towards the shield and the prosthesis, said part also limiting rotation of the cam.

Other objects and features of the invention will be apparent from the disclosure of this specification.

BRIEF DESCRIPTION OF THE DRAWINGS

One embodiment of the invention will now be described, by way of example only, with reference to the accompanying drawings, wherein:

FIG. 1 shows an acetabular prosthesis cemented into a subcondral acetabular recess;

FIG. 2 shows the prothesis of FIG. 1 in side elevation with a shield according to the invention disposed above it;

FIG. 3 is a plan view of the shield of FIG. 2;

FIG. 4 is a scrap section on line B—B of FIG. 3;

FIG. 5 shows the shield of FIG. 3 in an expanded condition;

FIGS. 6, 7 and 8 show tools for use in fitting the acetabular prosthesis, FIG. 7 being an elevation on arrow 7 of FIG. 6.

DETAILED DESCRIPTION OF THE INVENTION

Figure 8:
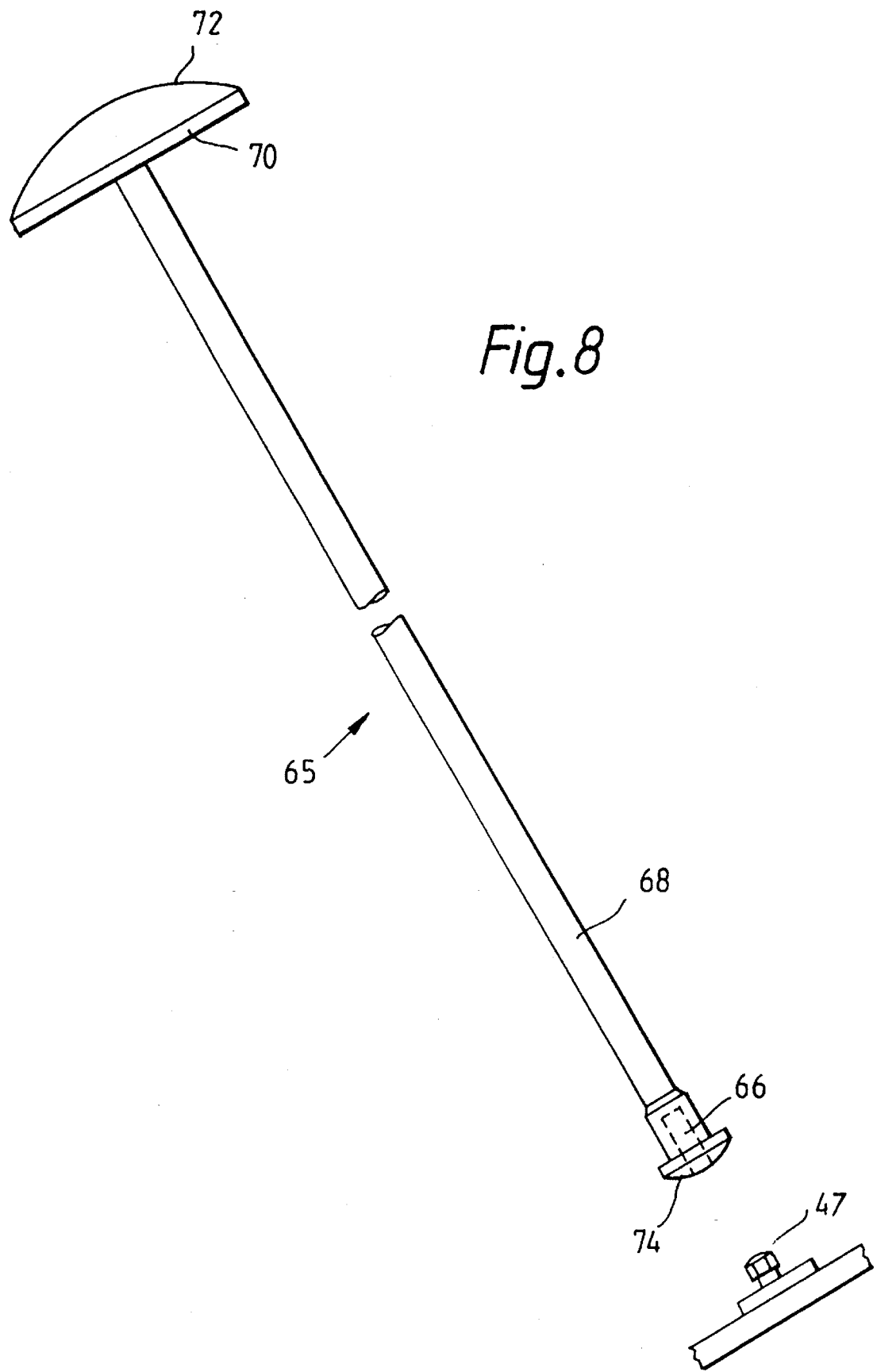

In FIG. 1, a subcondral acetabular recess 10 in pelvic bone 11 has received therein a prosthesis 12 having a socket 14 to accommodate a femoral prosthetic joint, as known in the art. The prosthesis 12 is cemented into the recess 10 by a suitable bone cement 13 eg. polymethylmethacrylate.

Referring to FIGS. 2 and 3, the prosthesis 12 is shown before insertion in the recess 10. It is provided with interrupted flanges 14 which key into the cement, as do prepared interdigitions and other irregularities in the cavity 10. However, for effective keying the cement must be adequately compressed before it is cured.

For this purpose, an adjustable shield 16 is located over the prosthesis 12 to retain the cement in the recess as described hereafter. The shield 16 consists of a first pair of generally semi-circular sections or leaves 18 and a second pair of similar sections 20. Each section 18, 20 is connected via snap-fit rivets 22 within slots 24 in each of the sections. The flanges 23 of the rivets 22 (see FIG. 4) are spaced sufficiently to permit free sliding and pivoting of the sections 18, 20 relative to each other to the extent permitted by the slots. The slots 24 are positioned orthogonally to diameters of the shield lying at 45° to inner edges 28,34 of the sections 18, 20 such that when the sections are closed-up as in FIG. 3 the slots lie on a circle centred on the centre of the shield.

The sections 20 have radially-extending slots 26 on the diameter perpendicular to their straight inner edges 28 (best seen in FIG. 5). The edges 28 have recesses 30 in their centre positions so as to define an aperture 32 when the edges 28 abut. The inner edges 34 of the sections 18 are relieved such that when the shield sections are closed-up the edges 34 are clear of the slots 26, and further arcuate cut-outs in the edges 34 also leave the aperture 32 exposed.

When the shield 16 is placed over the prosthesis 12 the slots 26 are aligned with two blind holes 36 in the top surface of the prosthesis. As described later, pegs of a locating and adjusting tool engage the holes 36 through the slots 26, locating the shield relative to the prosthesis. A cam of the locating tool is introduced into the aperture 32 and upon rotation forces the sections 20 outwards. The rivet and slot connections 22, 24 of the sections 20 to the other sections 18 cause the latter likewise to move outwards, orthogonally to the movement of the sections 20. The size of the generally planar disc-shaped shield 16 thus may be adjusted, the maximum extension of the FIG. 3 shield being shown in FIG. 5.

A tool 39 for adjusting and locating the shield 16 during fitting of the prosthesis 12 to an acetabulum is shown in FIGS. 6 and 7. The tool comprises a knurled handle 40 with an extension rod 42. At the end of the rod 42 is an angled plate 44 wherein is rotatably mounted a blade-like cam 46. The cam may be rotated by a male hexagonal boss 47 on the other side of the plate 44. Projecting from the plate 44 on the same side as the cam 46 are two pairs of pegs 48, 50. The cam and the pegs are positioned such that the pegs enter the slots 26 of the shield when the cam engages aperture 32 thereof.

The pegs 48 engage only the slots 26, but the pegs 50 are longer and pass through the slots to enter the holes 36 in the prosthesis, locating the shield relative thereto. The two pegs 48, 50 in each slot 26 constrain the sections 20 to move radially outwardly along the axis of the slots when adjusted.

The rod 42 is hollow and contains a shaft 52 which at its end 51 nearest the handle is biased by a spring 53 against a further cam 54 rotatably mounted about the axis of the handle 40. A knurled knob 56 is provided to facilitate rotation of the cam by the user's thumb whilst holding the handle 40.

At its other end the shaft 52 carries a plate 58 at the same angle as the plate 44. The plate 58 has an aperture 59 through which the cam 46 and pegs 48, 50 pass. A land 60 projects into the aperture 59 such that one surface 62 thereof provides a stop for the cam 46 when it is oriented to enter the aperture 32. A further surface 64 of the land limits rotation of the cam 46 to approximately 90° at which rotation the shield sections 18, 20 have been fully adjusted outwards.

Upon rotation of the further cam 54 the shaft 52 is extended, displacing the plate 58 away from the plate 44, as shown dotted in FIG. 6, whereby to disengage the adjusting and locating tool from the shield and the prosthesis.

FIG. 8 shows a tool 65 for applying compressive force to the bone cement and for rotating the cam 46. The tool comprises a female hexagonal socket 66 to engage the boss 47, carried by a shaft 68 terminating in an enlarged end 70 which the user may grasp to turn the cam 46. The end 70 also is shaped, with a curved upper surface 72 so that the user may apply pressure via the shaft 68 to the boss 47 and thence through the fixed plate 44 to the shield and the prosthesis.

In use, the subcondral acetabular cavity 10 is prepared in known manner and an appropriate quantity of bone cement is introduced therein.

The shield is placed on the cam and pegs 46, 48, 50 of the tool 39 followed by the prosthetic implant 12. The surgeon then introduces the prosthesis into the cavity 10, holding the tool 39 in one hand. Whilst holding the prosthesis in position with the tool 39, he attaches the tool 65 to the boss 47 and expands the shield 16 until it covers the edges of the acetabular cavity 10, and preferably also presses into surrounding soft tissue to form a seal. The bone cement is thus effectively contained in the cavity, and the surgeon then compresses it as necessary by applying axial force to the tool 65. Preferably, the force is maintained until the cement is sufficiently cured for the prosthesis to be firmly held. The tool 65 is then detached and the tool 39 disengaged from the shield 16 and prosthesis 12 by rotation of the cam 54. The consequent extension of the plate 58 steadies the shield and prosthesis, so that withdrawal of the cam 46 and pegs 48, 50 does not disturb the adhesion of the cement.

If desired the surgeon can apply further pressure to the prosthetic implant 12 by inserting the end 66 of the tool 65 directly into the socket 14 of the prosthesis, the surface 74 of the end 66 being shaped appropriately for this purpose.

Modifications may be made to the invention as above described, without departing from the spirit and scope of the invention, and therefore all matter herein described or shown in the drawings shall be interpreted as illustrative and not in a limiting sense.

What is claimed is:

1. An apparatus prosthetic system for use in fitting an acetabular prosthesis comprising in combination, a shield adapted to be positioned over a prosthesis to be placed in uncured bone cement in a subcondral acetabular recess, said shield being adjustable so as substantially to cover the recess and retain the cement therein whilst the cement is compressed to improve bonding of the prosthesis to the recess, the system further including an adjusting means for adjusting the size of the shield and compression means for compressing the cement, wherein the shield comprise a plurality of overlapping sections displaceable outwardly from the centre portion of the shield to adjust the size thereof and the adjusting means comprises a rotatable cam adapted to enter the centre portion of the shield.

2. The system as claimed in claim 1 wherein the shield is a substantially slat disc, the sections being slideably and pivotally connected to each other.

3. A system as claimed in claim 1, wherein the shield comprises apertures therein through which at least one fixed structure of the adjusting means passes and is adapted to engage an acetabular prosthesis, said fixed structure and apertures cooperating to locate the shield relative to the prosthesis.

4. A system as claimed in claim 3, wherein the compression means comprises means for rotating the cam and for applying force to the shield and the prosthesis via the fixed structure of the adjusting means.

5. A system as claimed in claim 4 comprising means for separating the adjusting means from the prosthesis and the shield after compression of the cement.

6. A system as claimed in claim 5 wherein the separating means comprises a part moveable away from the fixed structure towards the shield and the prosthesis, said part also limiting rotation of the cam.

7. The system of claim 1 wherein the connected overlapping displaceable sections are supported solely by each other.

8. In combination, an acetabular prosthesis and an apparatus for use in fitting the acetabular prosthesis, the apparatus comprising a shield configured to be positioned over the prosthesis, the prosthesis to be placed in uncured bone cement in a subcondral acetabular recess, said shield being adjustable so as substantially to cover the recess and retain the cement therein whilst the cement is compressed by seating the prosthesis within the recess to improve bonding of the prosthesis to the recess, wherein the shield comprises a plurality of overlapping sections displaceable outwardly from the center portion of the shield to adjust the size thereof, the combination further including adjusting means for adjusting the size of the shield and compression means for compressing the cement, the adjusting means comprises a rotatable cam adapted to enter the center portion of the shield.

9. The combination of claim 8, wherein the shield comprises apertures therein through which a fixed structure of the adjusting means passes and engages the acetabular prosthesis, said fixed structure and apertures cooperating to locate the shield relative to the prosthesis.

10. The combination of claim 9 wherein the compression means comprises means for rotating the cam and for applying force to the shield and the prosthesis through the fixed structure of the adjusting means.

11. The combination of claim 10 further comprising means for separating the adjusting means from the prosthesis and the shield after compression of the cement.

12. The combination of claim 11 wherein the separating means comprises a part moveable away from the fixed structure towards the shield and the prosthesis, said part also limiting rotation of the cam.

13. A method of fitting an acetabular prosthesis comprising placing bone cement in a subcondral acetabular recess, inserting the acetabular prosthesis therein, disposing an adjustable shield over the recess, adjusting the size of the shield substantially to cover the recess so as to contain the cement therein and seating the prosthesis by applying force to the prostheses through the shield wherein said cement is compressed during seating of the prosthesis and substantially retained within the cavity by the adjustable shield so as to improve bonding of the prosthesis to the recess wherein the adjustable shield is disposed over the prosthesis before it is inserted into the recess.

14. In combination, an acetabular prosthesis and an apparatus for use in fitting the acetabular prosthesis in uncured bone cement in a subcondral acetabular recess, the apparatus comprising a shield configured to be positioned over the recess and the prosthesis, said shield being adjustable so as substantially to cover the recess and retain the cement therein whilst the cement is compressed by seating the proshtesis within the recess to improve bonding of the prosthesis to the recess, wherein the shield comprises a plurality of overlapping sections dispaceable outwardly from the center portion of the shield to adjust the size thereof, the combination further including adjusting means for engaging and displacing the displaceable portions to adjust the size of the shield, and compression means for compressing the cement.

15. The combination of claim 14 wherein the adjusting means comprises a rotatable cam adapted to enter the center portion of the shield.

\* \* \* \* \*